US00PP23045P2

(12) United States Plant Patent
Beekenkamp

(10) Patent No.: US PP23,045 P2
(45) Date of Patent: Sep. 18, 2012

(54) ***CELOSIA* PLANT NAMED 'BKCELMG'**

(50) Latin Name: *Celosia hybrida*
Varietal Denomination: Bkcelmg

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 13/068,689

(22) Filed: May 17, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — C. A. Whealy

(57) ABSTRACT

A new and distinct cultivar of *Celosia* plant named 'Bkcelmg', characterized by its upright and compact plant habit; freely branching habit; dark green-colored leaves; freely flowering habit; red purple-colored flowers arranged on dense compound spikes; and good garden performance.

2 Drawing Sheets

Botanical designation: *Celosia hybrida.*
Cultivar denomination: 'BKCELMG'.

BACKGROUND OF THE INVENTION

The present invention relates to a new and distinct *Celosia* plant, botanically known as *Celosia hybrida* and hereinafter referred to by the name 'Bkcelmg'.

The new *Celosia* plant is a product of a planned breeding program conducted by the Inventor in Maasdijk, The Netherlands. The objective of the breeding program is to create new *Celosia* plants that have unique and attractive flowers, long flowering period and good garden performance.

The new *Celosia* plant originated from a cross-pollination in June, 2006 in Maasdijk, The Netherlands of a proprietary selection of *Celosia hybrida* identified as code number 1400009, not patented, as the female, or seed, parent with a proprietary selection of *Celosia hybrida* identified as code number 1401001, not patented, as the male, or pollen, parent. The new *Celosia* plant was discovered and selected by the Inventor as a single flowering plant from within the progeny of the stated cross-pollination in a controlled environment in Maasdijk, The Netherlands in August, 2007.

Asexual reproduction of the new *Celosia* plant by cuttings in a controlled environment in Maasdijk, The Netherlands since November, 2007 has shown that the unique features of this new *Celosia* plant are stable and reproduced true to type in successive generations.

SUMMARY OF THE INVENTION

Plants of the new *Celosia* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Bkcelmg'. These characteristics in combination distinguish 'Bkcelmg' as a new and distinct *Celosia* plant:

1. Upright and compact plant habit.
2. Freely branching habit.

3. Dark green-colored leaves.
4. Freely flowering habit.
5. Red purple-colored flowers arranged on dense compound spikes.
6. Good garden performance.

Plants of the new *Celosia* differ from plants of the female parent selection in the following characteristics:

1. Leaves of plants of the new *Celosia* are narrower and darker in color than leaves of plants of the female parent selection.
2. Plants of the new *Celosia* and the female parent selection differ in flower color as plants of the female parent selection have bright pink-colored flowers.

Plants of the new *Celosia* differ from plants of the male parent selection in the following characteristics:

1. Plants of the new *Celosia* are more compact than plants of the male parent selection.
2. Leaves of plants of the new *Celosia* are darker in color than leaves of plants of the male parent selection.
3. Plants of the new *Celosia* and the male parent selection differ in flower color as plants of the male parent selection have purple-colored flowers.

Plants of the new *Celosia* can be compared to plants of *Celosia* 'Caracas', not patented. In side-by-side comparisons, plants of the new *Celosia* differed primarily from 'Caracas' in the following characteristics:

1. Leaves of plants of the new *Celosia* were darker in color than leaves of plants of 'Caracas'.
2. Plants of the new *Celosia* flowered earlier than plants of 'Caracas'.
3. Plants of the new *Celosia* and 'Caracas' differed in flower color as plants of 'Caracas' had purple-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet comprises a side perspective view of a typical flowering plant of 'Bkcelmg' grown in a container.

The photograph on the second sheet is a close-up view of a typical flowering plant of 'Bkcelmg'.

DETAILED BOTANICAL DESCRIPTION

The aforementioned photographs and following observations, measurements and values describe plants grown in 11-cm containers during the early spring in a glass-covered greenhouse in Maasdijk, The Netherlands and under commercial practices. During the production of the plants, day temperatures ranged from 19° C. to 20° C. and night temperatures averaged 19° C. Plants were pinched one time and were 15 weeks old when the photographs and description were taken. In the following description, color references are made to The Royal Horticultural Society Colour Chart, 2007 Edition, except where general terms of ordinary dictionary significance are used.

Botanical classification: *Celosia hybrida* 'Bkcelmg'.

Parentage:

*Female, or seed, parent*.—Proprietary selection of *Celosia hybrida* identified as code number 1400009, not patented.

*Male, or pollen, parent*.—Proprietary selection of *Celosia hybrida* identified as code number 1401001, not patented.

Propagation:

*Type*.—By cuttings.

*Time to initiate roots, summer*.—About ten days at 20° C. to 21° C.

*Time to initiate roots, winter*.—About twelve days at 20° C. to 21° C.

*Time to produce a rooted young plant, summer*.—About 21 days at 20° C. to 21° C.

*Time to produce a rooted young plant, winter*.—About 24 days at 20° C. to 21° C.

*Root description*.—Medium in thickness, fibrous; white in color.

*Rooting habit*.—Moderate branching; medium density.

Plant description:

*Plant form and growth habit*.—Herbaceous annual typically grown as a potted plant; upright and compact plant habit; broad inverted triangle; freely branching habit with about seven lateral branches developing per plant; moderately vigorous growth habit.

*Plant height*.—About 29.1 cm.

*Plant width* (*spread*).—About 30.3 cm.

*Lateral branches*.—Length: About 15.8 cm. Diameter: About 6 mm. Internode length: About 9 mm. Texture: Smooth, glabrous. Color: Between 68A and 70B.

Foliage description:

*Arrangement*.—Alternate; simple.

*Length*.—About 8.2 cm.

*Width*.—About 3.6 cm.

*Shape*.—Ovate to narrowly ovate.

*Apex*.—Apiculate.

*Base*.—Attenuate.

*Margin*.—Entire.

*Texture, upper and lower surfaces*.—Smooth, glabrous.

*Venation pattern*.—Pinnate.

*Color*.—Developing leaves, upper surface: Between 143B and 144A. Developing leaves, lower surface: Close to 146C. Fully expanded leaves, upper surface: Between N137A and 147A; distal half, tinged with close to 200A; venation, close to 60C to 60D. Fully expanded leaves, lower surface: Close to 146B; distal half, tinged with close to 147A; venation, close to 60C.

*Petioles*.—Length: About 1.8 cm. Diameter: About 2.5 mm. Texture, upper and lower surfaces: Smooth, glabrous. Color, upper and lower surfaces: Close to 60D.

Flower description:

*Flower type and arrangement*.—Single sessile rotate flowers arranged in dense terminal compound spikes; flowers face upright and outwardly.

*Flowering habit*.—Freely flowering habit with about 2280 flowers per inflorescence.

*Fragrance*.—Faint, slightly moldy.

*Natural flowering season*.—Plants begin flowering about ten weeks after planting; flowering continuous from early April until the autumn in The Netherlands.

*Postproduction longevity*.—Inflorescences last about ten days on the plant; flowers not persistent.

*Inflorescence height*.—About 11.6 cm.

*Inflorescence diameter*.—About 7.2 cm.

*Flower diameter*.—About 6 mm.

*Flower height*.—About 6 mm.

*Flower buds*.—Length: About 6 mm. Diameter: About 1.5 mm. Shape: Ovoid. Color: Close to 71C.

*Petals*.—None observed.

*Sepals*.—Quantity per flower: Typically eight. Length: About 6 mm. Width: About 1.5 mm. Shape: Narrowly ovate. Apex: Narrowly acute. Margin: Entire. Texture, upper and lower surfaces: Smooth, glabrous. Color: When opening and fully opened, upper surface: Close to 71C; color does not change with development. When opening and fully opened, lower surface: Close to 71C; color does not change with development.

*Peduncles*.—Length: About 11.2 mm. Diameter: About 4 mm. Angle: Upright to about 30° from vertical. Strength: Moderately strong. Texture: Smooth, glabrous. Color: Close to 63B.

*Reproductive organs*.—Stamens: Quantity per flower: Typically five. Filament length: Close to 3 mm. Filament color: Close to 61A; towards the base, close to 61C to 61D. Anther length: About 1 mm. Anther shape: Lanceolate. Anther color: Close to 71C. Pollen amount: Scarce. Pollen color: Close to 156A. Pistils: Quantity per flower: One. Length: About 4 mm. Stigma shape: Club-shaped. Stigma color: Close to 71C. Style length: About 3.5 mm. Style color: Close to 71C to 71D; towards the base, close to 61C to 61D. Ovary color: Close to 71C to 71D.

*Seeds and fruits*.—Seed and fruit development have not been observed on plants of the new *Celosia*.

Disease/pest resistance: Plants of the new *Celosia* have not been noted to be resistant to pathogens and pests common to *Celosia*.

Garden performance: Plants of the new *Celosia* have been observed to have good garden performance and have good tolerance to rain and wind. Plants of the new *Celosia* have been observed to tolerate high temperatures of about 35° C. and to be hardy to USDA Hardiness Zone 9.

It is claimed:

1. A new and distinct *Celosia* plant named 'Bkcelmg' as illustrated and described.

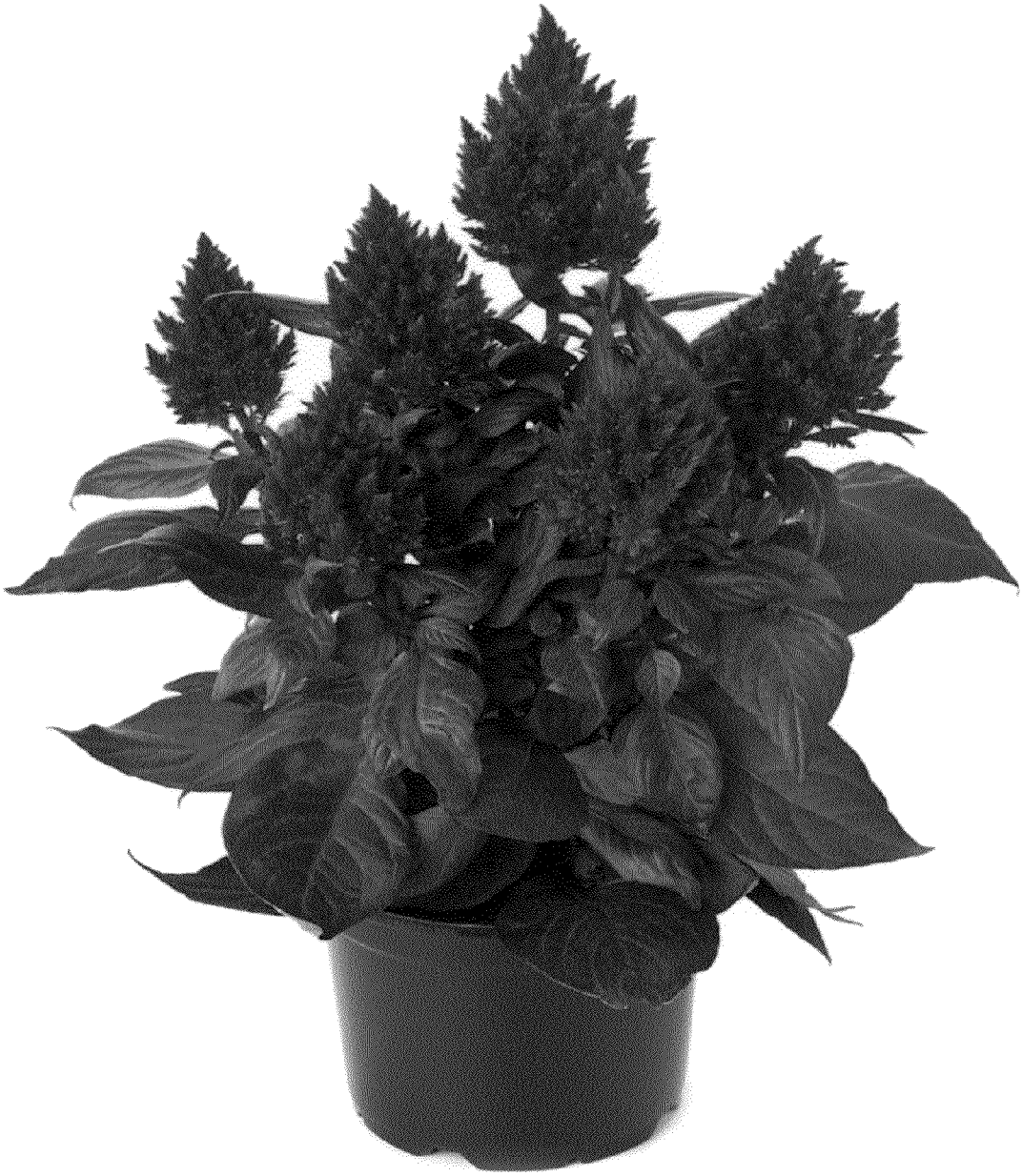

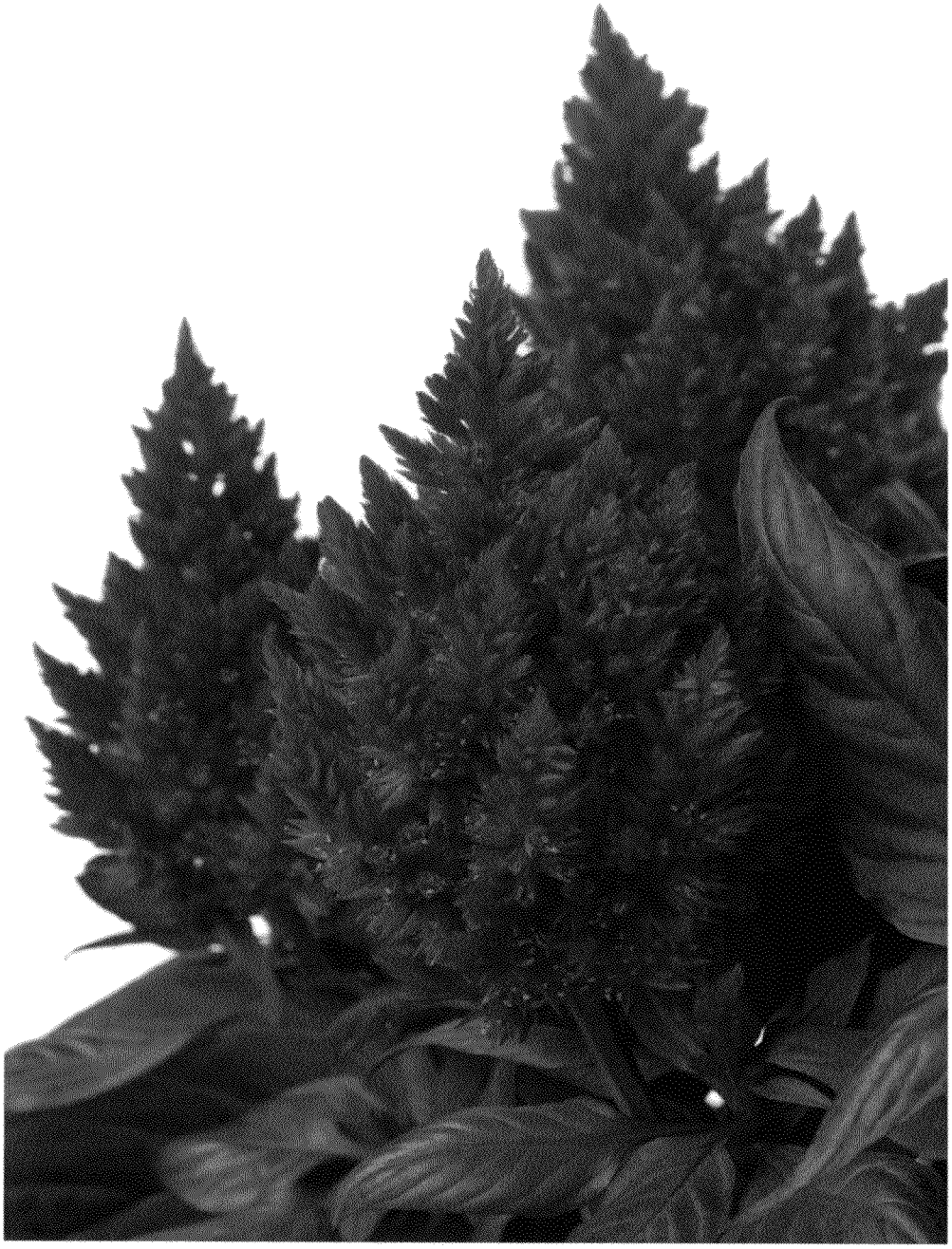

* * * * *